(12) United States Patent
Matsui

(10) Patent No.: US 8,088,966 B2
(45) Date of Patent: Jan. 3, 2012

(54) ABSORBENT ARTICLE

(75) Inventor: Tomotsugu Matsui, Ehime (JP)

(73) Assignee: Daio Paper Corporation, Shikokuchuo-Shi (JP)

( * ) Notice: Subject to any disclaimer, the term of this patent is extended or adjusted under 35 U.S.C. 154(b) by 0 days.

(21) Appl. No.: 10/593,173

(22) PCT Filed: Mar. 11, 2005

(86) PCT No.: PCT/JP2005/004844
§ 371 (c)(1),
(2), (4) Date: Sep. 15, 2006

(87) PCT Pub. No.: WO2005/087163
PCT Pub. Date: Sep. 22, 2005

(65) Prior Publication Data
US 2007/0197986 A1    Aug. 23, 2007

(30) Foreign Application Priority Data
Mar. 16, 2004    (JP) .................. 2004-074101

(51) Int. Cl.
*A61F 13/15*    (2006.01)

(52) U.S. Cl. ......... 604/361; 604/364; 604/367; 604/378

(58) Field of Classification Search .............. 604/361, 604/364, 367, 378, 358
See application file for complete search history.

(56) References Cited

U.S. PATENT DOCUMENTS

| | | | | |
|---|---|---|---|---|
| 4,022,211 | A * | 5/1977 | Timmons et al. | 604/361 |
| 4,287,153 | A * | 9/1981 | Towsend | 422/56 |
| 5,035,691 | A * | 7/1991 | Zimmel et al. | 604/361 |
| 5,354,289 | A * | 10/1994 | Mitchell et al. | 604/361 |
| 5,468,236 | A * | 11/1995 | Everhart et al. | 604/361 |
| 5,766,212 | A * | 6/1998 | Jitoe et al. | 604/361 |
| 5,902,669 | A * | 5/1999 | Steinhardt et al. | 428/198 |
| 5,947,943 | A | 9/1999 | Lee | |
| 6,307,119 | B1 * | 10/2001 | Cammarota et al. | 604/361 |
| 6,506,958 | B2 * | 1/2003 | Williams | 604/361 |
| 6,576,810 | B1 * | 6/2003 | Underhill et al. | 604/361 |
| 6,657,099 | B1 * | 12/2003 | Underhill et al. | 604/361 |
| 6,747,185 | B2 * | 6/2004 | Inoue et al. | 604/361 |
| 6,815,207 | B2 * | 11/2004 | Yabuki et al. | 436/2 |
| 7,002,054 | B2 * | 2/2006 | Allen et al. | 604/361 |
| 7,154,019 | B2 * | 12/2006 | Mishima et al. | 604/361 |
| 7,159,532 | B2 * | 1/2007 | Klofta et al. | 116/206 |

(Continued)

FOREIGN PATENT DOCUMENTS

EP    0776645 A1    6/1997
(Continued)

OTHER PUBLICATIONS

EP Search Report dated Jun. 21 2011 for EP05721031.2.

*Primary Examiner* — Jacqueline F. Stephens
(74) *Attorney, Agent, or Firm* — Sughrue Mion, PLLC

(57) ABSTRACT

An absorbing article which comprises a liquid permeable top sheet, an absorbing material, a moisture permeable waterproof sheet and a back sheet impermeable to a liquid, being integrated in the above order, wherein an aqueous component indicator comprising a hydrophilic resin coating layer and a notification mark provided on the inner surface of said hydrophilic resin coating layer is provided on the inner surface of the above moisture permeable waterproof sheet.

8 Claims, 8 Drawing Sheets

U.S. PATENT DOCUMENTS

| | | | |
|---|---|---|---|
| 7,241,627 B2 * | 7/2007 | Wilhelm et al. | 436/518 |
| 7,285,160 B2 * | 10/2007 | Zhu et al. | 106/31.58 |
| 7,306,764 B2 * | 12/2007 | Mody | 422/58 |
| 7,332,642 B2 * | 2/2008 | Liu | 604/361 |
| 2001/0006867 A1 * | 7/2001 | Suekane et al. | 442/394 |
| 2002/0061595 A1 * | 5/2002 | Yabuki et al. | 436/39 |
| 2002/0095126 A1 * | 7/2002 | Inoue et al. | 604/361 |
| 2003/0014025 A1 * | 1/2003 | Allen et al. | 604/361 |
| 2003/0045845 A1 * | 3/2003 | Yoshioka | 604/361 |
| 2003/0148091 A1 * | 8/2003 | Ikeda et al. | 428/317.9 |
| 2003/0154904 A1 * | 8/2003 | Klofta et al. | 116/206 |
| 2003/0164136 A1 * | 9/2003 | Klofta et al. | 116/206 |
| 2005/0234414 A1 * | 10/2005 | Liu | 604/361 |
| 2006/0229578 A1 * | 10/2006 | Roe et al. | 604/361 |

FOREIGN PATENT DOCUMENTS

| | | |
|---|---|---|
| EP | 1287799 A2 | 3/2003 |
| JP | 09-299401 | 11/1997 |
| JP | 2002-153505 | 5/2002 |
| JP | 2003-516185 | 5/2003 |
| JP | 2003-210522 | 7/2003 |
| JP | 2003-070838 | 11/2003 |
| WO | 00/76443 A1 | 12/2000 |
| WO | 01/41691 A1 | 6/2001 |
| WO | 01/94845 A1 | 12/2001 |

* cited by examiner

ABSORBENT ARTICLE

BACKGROUND OF THE INVENTION

1. Technical Field

This invention relates to an absorbent article such as a disposable paper diaper, a sanitary napkin or the like, and more particularly to an absorbent article provided with an indicator means capable of identifying an excretion of body fluid such as urine or the like from an outer side.

2. Background Art

An absorbent article such as a disposable paper diaper, a sanitary napkin or the like, should provide a quality giving amenity to a wearer and usability to the user. In order to obtain the amenity, a water vapor permeable film is generally employed in this field. The level of water vapor permeability has become higher and higher from year to year. Further, in order to improve the usability, an indicator means informing the user (for example, a mother) of the excretion of the body fluid of the wearer (for example, a nursling) is in heavy usage. As the indicator means, there has been developed a water content indicator which quickly responds with a small amount of water content.

Previously, as the water content indicator provided in the absorbent article as mentioned above, there has been generally known an absorbent article in which a display element constituted by a water based ink or paint discolored by the water content is directly applied to an inner surface (that is, a skin contact surface) side of a base material sheet constituted by an unpigmented hydrophilic paper (refer, for example, to Japanese Unexamined Patent Publication No. 9-299401), or an absorbent article in which a hydrophilic composition discolored by a change of pH on the basis of the water content is directly applied to an inner surface of a liquid impermeable back sheet (refer, for example, to Japanese Unexamined Patent Publication No. 2003-210522).

However, in the conventional absorbent article provided with the water content indicator mentioned above, for example, in the case that it is stored in a warehouse at a time of transporting, or in the case that it is displayed at the store or the like, it has been a problem that the absorbent article is exposed to the outside air and the outside light, and the water content indicator is already reacted and discolored before being used. If the water content indicator is reacted and discolored before being used as mentioned above, it is hard to identify from the outer side whether or not the excretion of body fluid is actually executed. Further, in the case that a small amount of body fluid is excreted, it is more difficult to identify the excretion.

This invention has been made under the circumstances as described above, and its object is to provide an absorbent article which removes the defect of the absorbent article as mentioned above, which prevents the function from decreasing even if it is exposed to the outside air and the outside light in the transportation or the storage or the like, which is provided with a high sensitive water content indicator which can immediately identify the excretion from the outer side even if it is a small amount of body fluid, and which gives an amenity to a wearer and a usability to a user.

SUMMARY

The above object of this invention is attained by providing an absorbent article structured by integrally forming at least a liquid permeable top sheet, an absorbent, a water vapor permeable waterproof sheet, and a liquid impermeable back sheet in this order, characterized in that a water content indicator is provided on an inner surface of the water vapor permeable waterproof sheet, the water content indicator being constituted by a hydrophilic resin coating layer and an information mark provided on an inner surface of the hydrophilic resin coating layer.

The above object of this invention is more effectively attained by providing an absorbent article characterized in that the water vapor permeable waterproof sheet is constituted by a sheet material in which a water vapor permeability on the basis of JIS Z-0208 method of test is 700 g/m$^2$/24 h or more.

The above object of this invention is more effectively attained by providing an absorbent article characterized in that the hydrophilic resin coating layer constituting the water content indicator and the information mark are formed in approximately same shape.

Moreover, the above object of this invention is effectively attained by providing an absorbent article characterized in that a print surface by a general ink is provided at a position corresponding to the information mark between the water vapor permeable waterproof sheet and the hydrophilic resin coating layer.

As mentioned above, the absorbent article of this invention is provided with the water content indicator constituted by the hydrophilic resin coating layer having a moisture resistance on the inner surface of the waterproof sheet having the high water vapor permeability, and the information mark formed on the inner surface of the hydrophilic resin coating layer. Therefore, according to the absorbent article of this invention, a stuffy state is not generated even if the wearer has the absorbent article on, owing to the water vapor permeable waterproof sheet having the high water vapor permeability, whereby it is possible to give the amenity to the wearer. Further, since the provided water content indicator has the moisture resistance, the function of the water content indicator is not deteriorated by the humidity of the outside air. Furthermore, since the water content indicator has the high sensitivity, there can be provided with the absorbent article having a very high usability for the user, that the water content indicator is rapidly reacted and changed by the body fluid even if the amount of excretion of the body fluid is extremely small, whereby it is possible to immediately inform the user of the excretion.

In this case, the moisture resistance in this invention means that the water vapor permeability, which the waterproof sheet essentially has, is lowered by coating the resin on the waterproof sheet, in the case that the water vapor permeability is measured on the basis of JIS Z-0208 method of test. In accordance with experiment of this inventor, if PVA resin of 10 µm is coated on the waterproof sheet which the water vapor permeability is 9000 g/m$^2$/24 h, it appears that the water vapor permeability is lowered to 1500 g/m$^2$/24 h. As described later, it is preferable that the water vapor permeable waterproof sheet is constituted by a sheet material in which the water vapor permeability on the basis of JIS Z-0208 method of test is 700 g/m$^2$/24 h or more, particularly 7000 g/m$^2$/24 h or more. Further, in accordance with this absorbent article on the basis of the structure mentioned above, there is obtained a pronounced effect that the water content indicator is reacted and changed for an extremely short time within 10 second, even in the case that a small amount, for example, 10 cc of urine is excreted.

DETAILED DESCRIPTION OF THE EXEMPLARY EMBODIMENTS

A description will be in detail given below of contents of this invention by exemplifying a case that an absorbent article is constituted by a disposable paper diaper. In this case, it is needless to say that this invention is not necessarily limited to this example, but that variations may be made without departing from the scope of claims.

Figure 1:
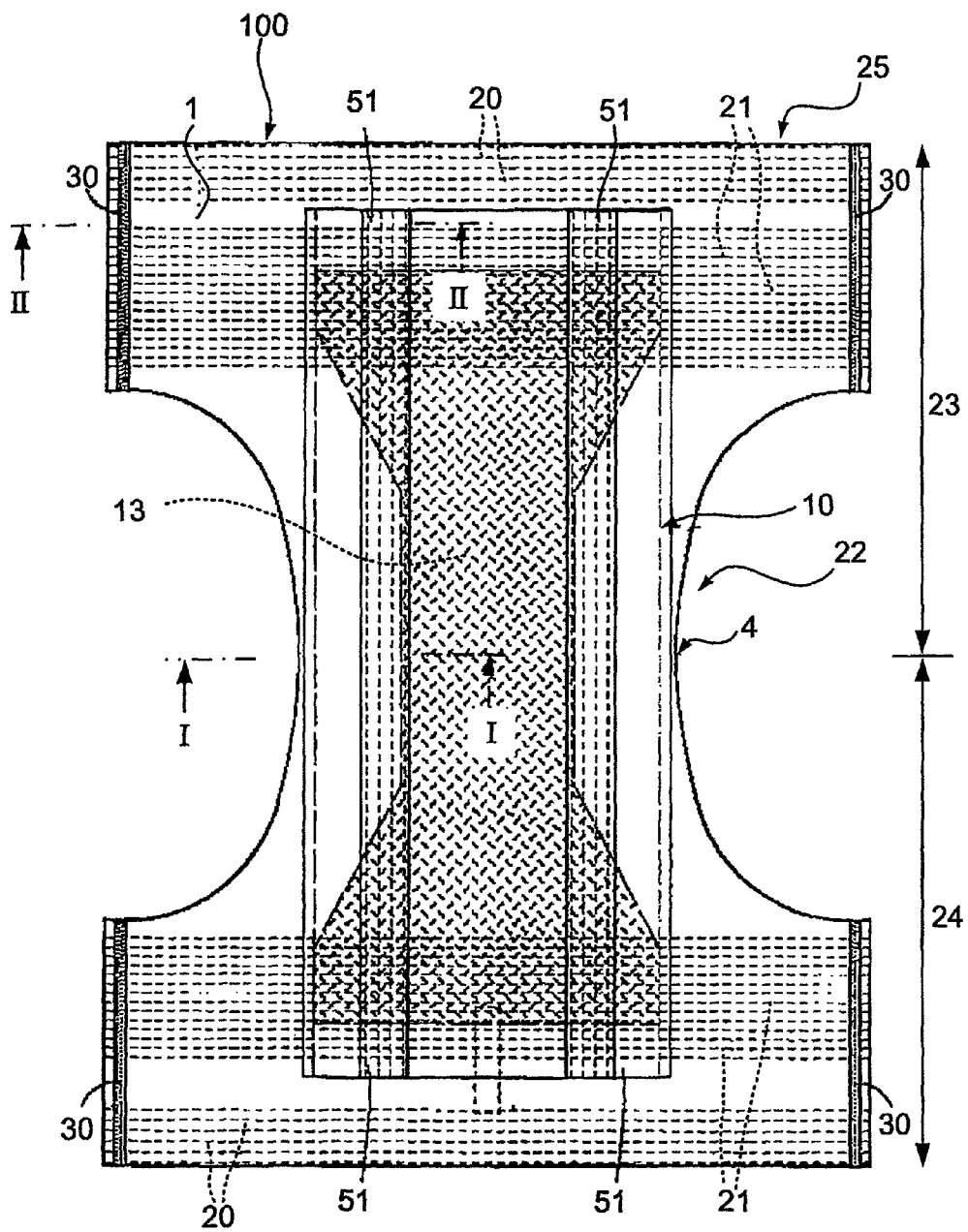
FIG. 1 is an expansion plan view of a disposable paper diaper in accordance with a first embodiment of this invention.
Figure 2:
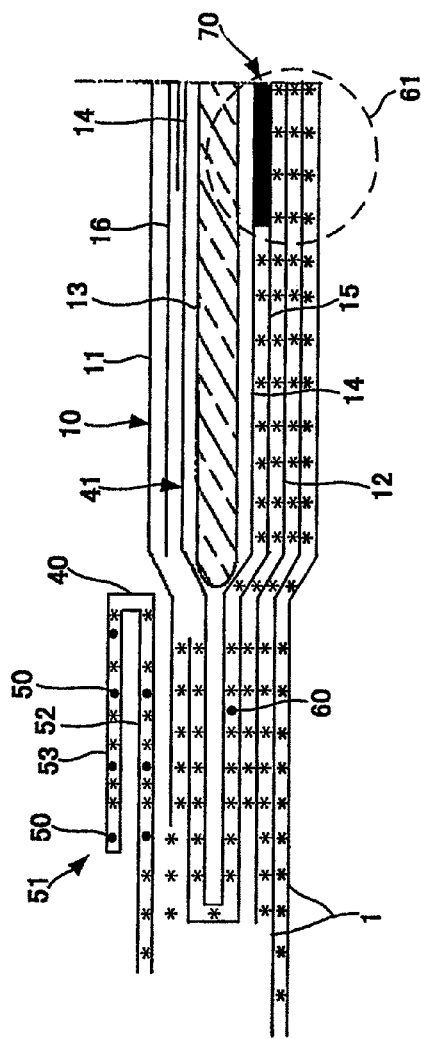
FIG. 2 is a sectional view taken along the line I-I of FIG. 1.
Figure 3:
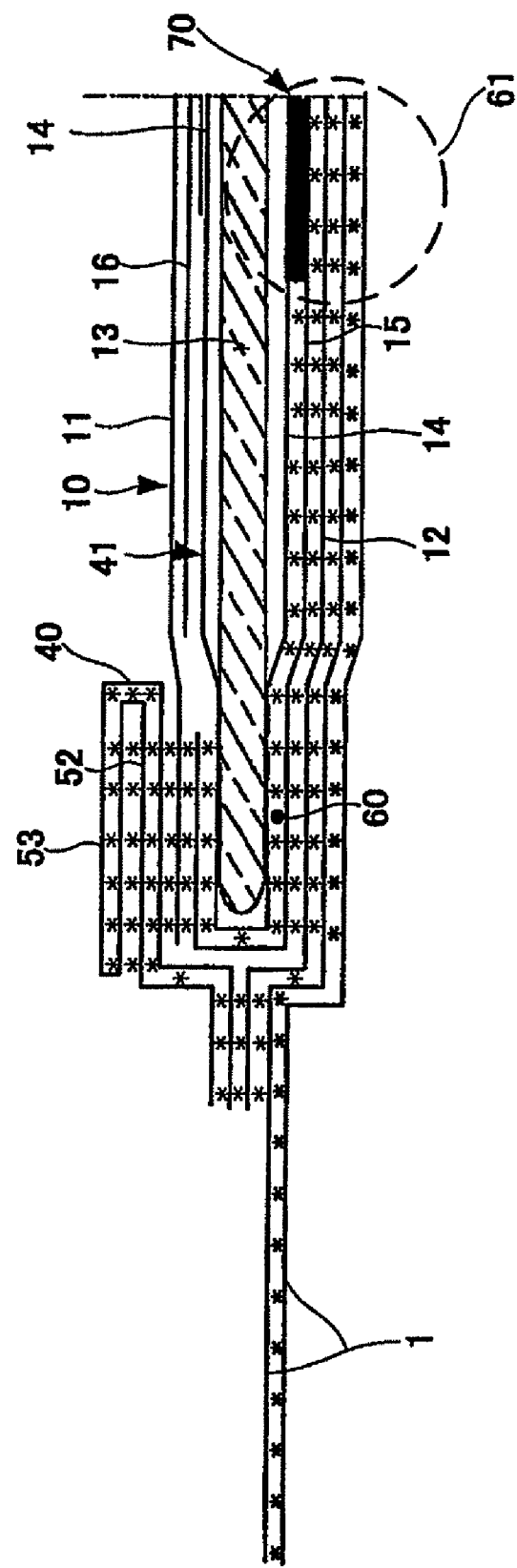
FIG. 3 is a sectional view taken along the line II-II of FIG. 1.

FIG. 1 shows a first embodiment of this invention, and it is a plan view in the case of expanding a pants type disposable paper diaper (hereinafter, refer to as "present paper diaper") 100 and viewing it from a front face side, FIG. 2 is a sectional view taken along the line I-I of FIG. 1, and FIG. 3 is a sectional view taken along the line II-II of FIG. 1.

The present paper diaper 100 is formed by adhering and fixing an absorbent main body 10 integrated by adhering a rectangular liquid permeable top sheet 11, an absorbing element 41 formed by covering a sandglass-shaped absorbent 13 with a crepe paper 14, a rectangular water vapor permeable waterproof sheet 15, and a liquid impermeable back sheet 12 by a hot melt adhesive agent or the like in this order (reference sign * in the drawing denotes an adhered portion) to a front face side of a flexible outline sheet 1. In this case, a liquid permeable second sheet 16 is interposed between the liquid permeable top sheet 11 and the absorbing element 41. In this case, for the purpose of increasing a fitting property around a hipline and preventing a body fluid from leaking out from a longitudinal direction, a waist elastic stretchable member 20 and a hipline elastic stretchable member 21 are provided, and in order to prevent body fluid from leaking out from a legline opening portion 22, there is formed a rising cuff 51 (this rising cuff 51 is constituted by a rising portion 52 and a flat surface contact portion 53 as depicted in FIG. 2). The rising cuff 51 is disposed around a leg protruding to a front face side by a rising sheet 40 continuously provided in a width direction and elastic stretchable members 50 and 60. With reference to FIG. 2, a riding end 54 is also shown.

The outline sheet 1 provided with the absorbent main body 10 is structured such that a front body side 23 and a back body side 24 are folded around a crotch portion 4 in a post-process of production, and both side edge portions 30 in a longitudinal direction are adhered by means of an ultrasonic sealing, a thermal welding or the like. Accordingly, a waistline opening portion 25 and a legline opening portion 22 are formed, whereby the pants type disposable paper diaper 100 is completed (a completion drawing is not illustrated).

In this case, the outline sheet 1 is formed by laminating two transparent to semitransparent laminated unwoven fabric cloths or the like having an air permeability and a water repellancy. Further, since the top sheet 11 directly touches with a skin of a wearer, the top sheet 11 preferably employs an unwoven fabric cloth, or a porous plastic sheet or the like having a pleasant feel. The absorbent 13 may employ any material as far as it can absorb and hold body fluid, in general. The absorbent 13 employs a material in which an absorbent main body is obtained by mixing an absorbable polymer to a cotton-like pulp and the absorbent main body is formed in a sandglass shape having a certain thickness and rigidity. The absorbing element 41 is obtained by covering an entire outer peripheral surface of the absorbent main body with a crepe paper 14 having flexibility and liquid permeability. The water vapor permeable waterproof sheet 15 mentioned below is provided together with the liquid impermeable back sheet 12 in such a manner as to cover both side portions of a surface wrapping from a back face to a front face side of the absorbing element 41.

The back sheet 12 employs a sheet material having at least a water shielding property such as a transparent to semitransparent polyethylene, polypropylene or the like, and additionally employs a laminated unwoven fabric cloth obtained by laminating the unwoven fabric cloth on the polyethylene sheet or the like. Further, a filamentous elastic rubber constituted by a styrene family rubber, an olefin family rubber, a urethane family rubber, a polyurethane, a polystyrene or the like is preferably employed as a raw material of the elastic stretchable members 20, 21, 50 and 60 for the respective intended uses mentioned above.

A micro porous sheet or the like is preferably employed for the water vapor permeable waterproof sheet 15 used in the present paper diaper 100, from the point of view of preventing leakage of body fluid and a stuffy state. The micro porous sheet is obtained by melting and kneading an inorganic filler into a material having water shielding property and water vapor permeability, for example, an olefin resin such as a polyethylene, a polypropylene or the like so as to form a sheet, and thereafter centrifuging in a uniaxial or biaxial direction. Further, it is possible to employ a material obtained by directly coating an acryl resin, a polyurethane resin or the like on a base material such as an unwoven fabric cloths or the like.

In this case, in accordance with an experiment, taking into consideration amount of sweating of the wearer, a sheet material in which a water vapor permeability on the basis of JIS Z-0208 method of test is 700 g/m$^2$/24 h or more is preferable for the water vapor permeable waterproof sheet 15, and in order to keep a comfortable environment particularly after a violent movement or passing urine, a sheet material in which the water vapor permeability is 7000 g/m$^2$/24 h or more is most preferable.

Figure 4:
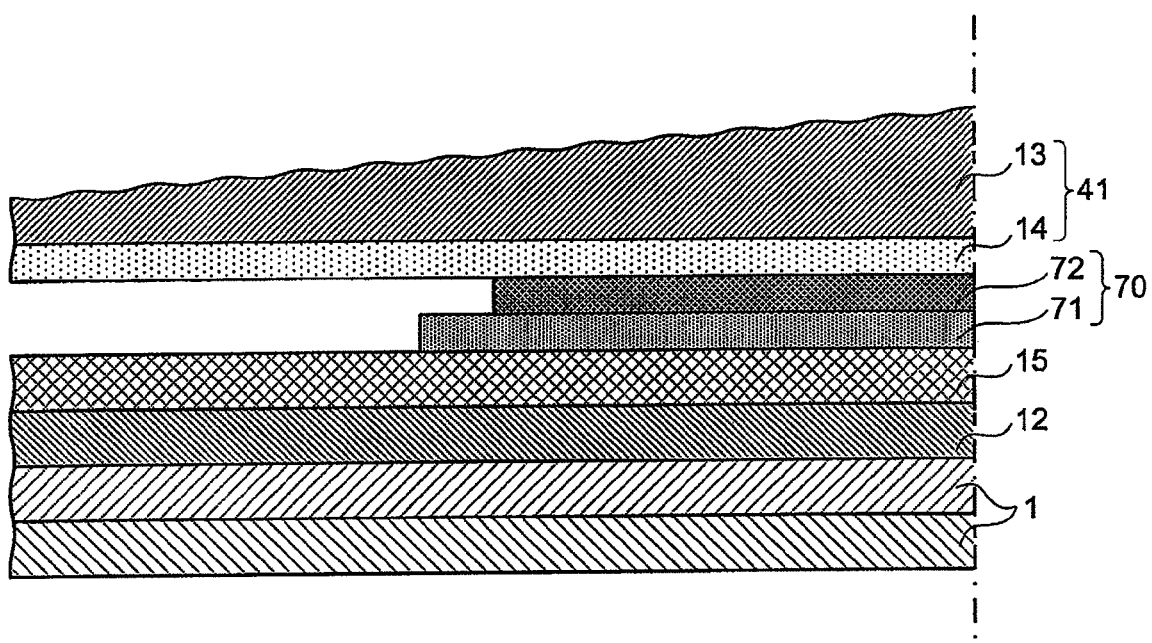
FIG. 4 is an enlarged cross sectional view of the main portion of the first embodiment.

In the present paper diaper 100, on an inner surface of the water vapor permeable waterproof sheet 15, a water content indicator 70 informing of an excretion of body fluid is provided at least near a center line of the absorbent 13 within a range of being covered by the absorbent 13. The water content indicator 70 is shown by a black cross section in FIGS. 2 and 3. The water content indicator 70 is constituted by a hydrophilic resin coating layer 71 and an information mark 72 provided on an inner surface of the hydrophilic resin coating layer 71, as shown in FIG. 4 by enlarging a cross section of a main portion (a portion shown by a dotted line circle 61 in FIGS. 2 and 3).

The hydrophilic resin coating layer 71 is formed by coating a coating liquid of hydrophilic resin, for example, CMC, PVA, PEO, poly acrylic sodium or the like on an inner surface of the waterproof film 15 at a thickness of about 1 to 20µ in accordance with a known coating system, for example, a gravure coater or the like. The hydrophilic resin mentioned above is further desirable such that a weather resistance is increased by adding to the hydrophilic resin coating layer 71 an ultraviolet absorbent such as those in the salicylic acid family, benzophenone family, benzotriazole family, cyanoacrylate family, or the like; an ultraviolet scattering agent such as zinc oxide, titanium oxide or the like; and/or a light stabilizer such as hindered amine family or the like, antioxidant such as ascorbic acid or the like. In this case, if the layer thickness is too large, the portion, which is thick becomes undesirably hard and feels unpleasant.

The information mark 72 is formed by coating a known coating liquid for a water content indicator on the inner surface of the hydrophilic resin coating layer 71 at a thickness between 1 and 20μ by a known coating machine in the same manner as mentioned above. The known coating liquid for water content indicator is constituted, for example, by an erasing ink colored from an achromatic color to a specific color of a coloration chemical compound on the basis of a molecular contact by one kind or more electron donating a coloration chemical compound selected from crystal violet lactone, malachite green lactone or the like with an electron accepting property developed color chemical compound corresponding to organic acid or organic acid salt such as citric acid, itaconic acid, salicylic acid, zinc salicylate or the like, and decolored only by an attachment of the water, a water soluble ink using a food color such as a blue No. 1 or the like, or a hot melt adhesive agent composition formed so as to include an indicator such as promophenol blue, methyl red or the like discolored in response to a change of pH control component and pH. In this case, if the thickness of the information mark 72 is too small, it is hard to be viewed from the outer side. On the contrary, if the thickness is too large, the amount of the coating liquid is increased, and a manufacturing cost is increased. Accordingly, it is preferable to set the thickness in the range mentioned above.

Figure 5:
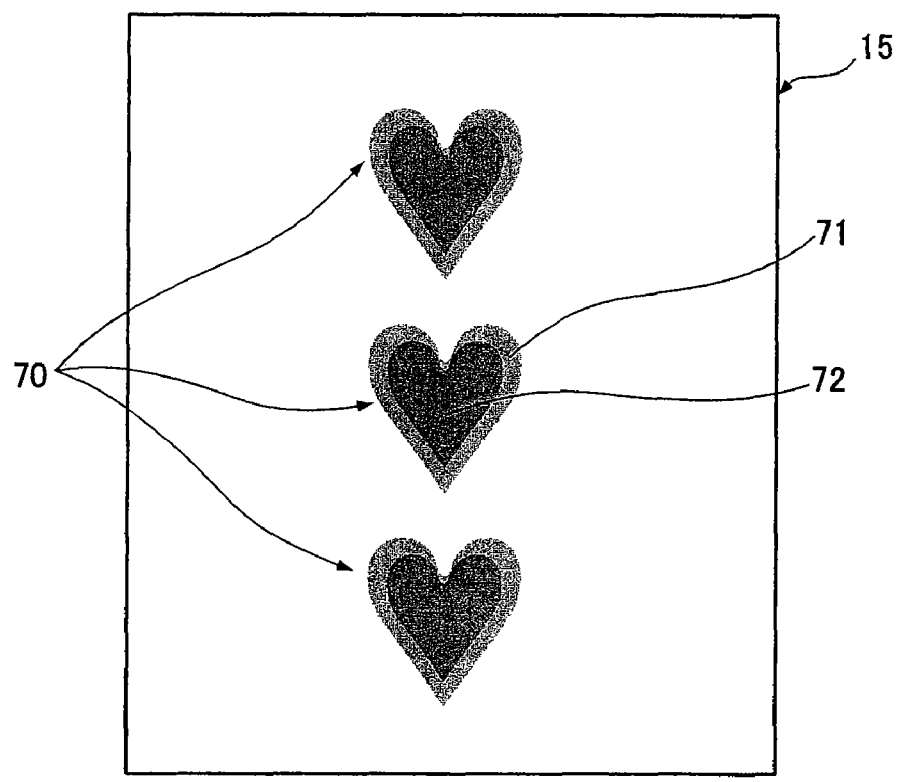
FIG. 5 is a plan view of the main portion of the first embodiment.

FIG. 5 is a plan view showing a flat surface shape of the water content indicator 70 constituted by the hydrophilic resin coating layer 71 and the information mark 72.

As illustrated, the flat surface shape of the water content indicator 70 shows a state in which the information mark 72 is formed on the inner surface of the hydrophilic resin coating layer 71 in a heart-shaped pattern arranged at even intervals in a longitudinal direction of the center portion of the water vapor permeable waterproof sheet 15 in such a manner as to be included within the heart-shaped pattern and have approximately the same shape. When viewing the water content indicator 70 structured as mentioned above from the outer side via the transparent to semitransparent back sheet 12 and the outline sheet 1, it appears as though the design is applied to the present paper diaper 100, and there is an advantage that a beauty is given to the viewer.

Further, if the outer shape of the hydrophilic resin coating layer 71 is brought into line with the outer shape of the information mark 72 as mentioned above, it is possible to minimize the required amount of the hydrophilic resin coating liquid forming the hydrophilic resin coating layer 71, whereby it is possible to reduce the manufacturing cost of the present paper diaper 100.

In this case, the information mark 72 is not limited to the heart-shaped pattern as mentioned above, but can be appropriately selected in correspondence to the purpose from the conventionally known various patterns, for example, a letter, mark, design, or combination thereof or the like.

In accordance with the present paper diaper 100 provided with the water content indicator 70 as mentioned above, if the body fluid, for example urine, is excreted to the surface of the liquid permeable top sheet 11, urine is diffused and moved so as to be absorbed within the absorbing element 41. However, at this time, if urine acts on the water content indicator 70 adjacent to the absorbing element 41 although it is at a trace quantity, the information mark 72 is immediately discolored or decolored in response to the water content included in this urine. Accordingly, the user can immediately recognize the change of the information mark 72 from the outer side via the transparent to semitransparent back sheet 12 and the outline sheet 1.

In this case, in accordance with an experiment, it is confirmed that the water content indicator 70 is reacted and discolored within a short time, for example ten second, in response to an extremely small amount of urine, for example, 10 cc urine. In this case, the water content indicator 70 is provided in the present paper diaper 100 having the absorbent 13 formed by uniformly mixing the pulp and the SAP in such a manner that respective weights come to 200 $g/m^2$ and 150 $g/m^2$.

Further, as mentioned above, since the hydrophilic resin coating layer 71 constituting the water content indicator 70 has an excellent property in terms of the moisture resistance, the water content indicator 70 is neither reacted nor discolored even if the present paper diaper 100 is exposed to the outside air over the long term, and it is possible to maintain the function long.

Further, in the present paper diaper 100, since the water vapor permeable waterproof sheet 15 employs the sheet material having the excellent water vapor permeability in which the water vapor permeability on the basis of JIS Z-0208 method of test is 700 $g/m^2/24$ h or more, most preferably 7000 $g/m^2/24$ h or more, the stuffy state is not generated in the crotch portion even if the wearer wears it for a long time. Further, since it feels pleasant, it is possible to apply the comfortable feeling to the wearer.

In this case, the present paper diaper 100 in accordance with the first embodiment of this invention described above is provided with the second sheet 16 and the outline sheet 1, however, these sheet members are not always necessary, but can be omitted in accordance with configuration, purpose, application or the like of the absorbent article.

Further, as the system for forming the hydrophilic resin coating layer on the inner surface of the water vapor permeable waterproof sheet, or the system for forming the information mark on the inner surface of the hydrophilic resin coating layer, it is possible to employ in addition to the gravure printing, an offline printing system, for example, flexographic printing or the like, or an inline printing system on the basis of ink jet, hot melt or the like.

Figure 6:
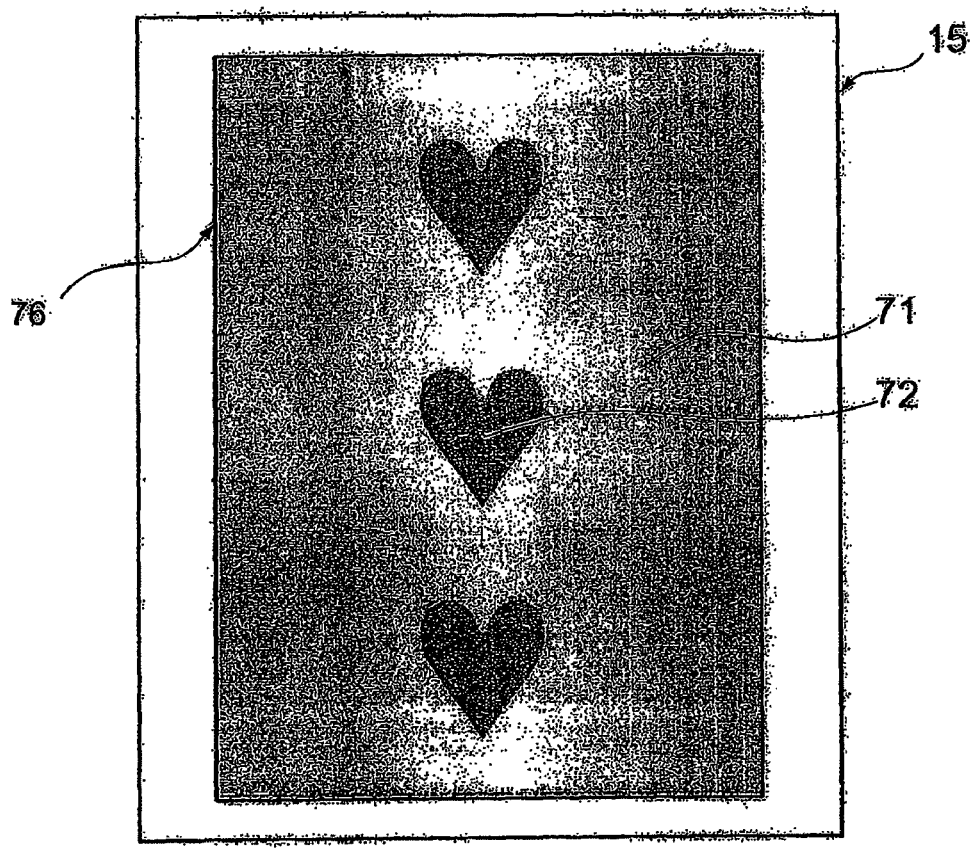
FIG. 6 is a plan view of the main portion of the second embodiment in accordance with this invention.

FIG. 6 shows a main portion of a second embodiment in accordance with this invention, and in particular, it is a plan view of a water content indicator 76 in accordance with a modified embodiment of the water content indicator 70 provided in the present paper diaper 100.

As illustrated, the water content indicator 76 is structured such that the hydrophilic resin coating layer 71 is formed in a rectangular shape over an approximately entire surface of the water vapor permeable waterproof sheet 15, and the information marks 72 having the same shape and thickness as mentioned above are provided in the inner surface thereof. In the case that the hydrophilic resin coating layer 71 is set wider as mentioned above, and the information mark 72 is provided on the hydrophilic resin coating layer 71, it is possible to obtain the same effect as mentioned above, apart from cost problems, and there can be also obtained an advantage that marks of various forms can be set in large numbers.

Figure 7:
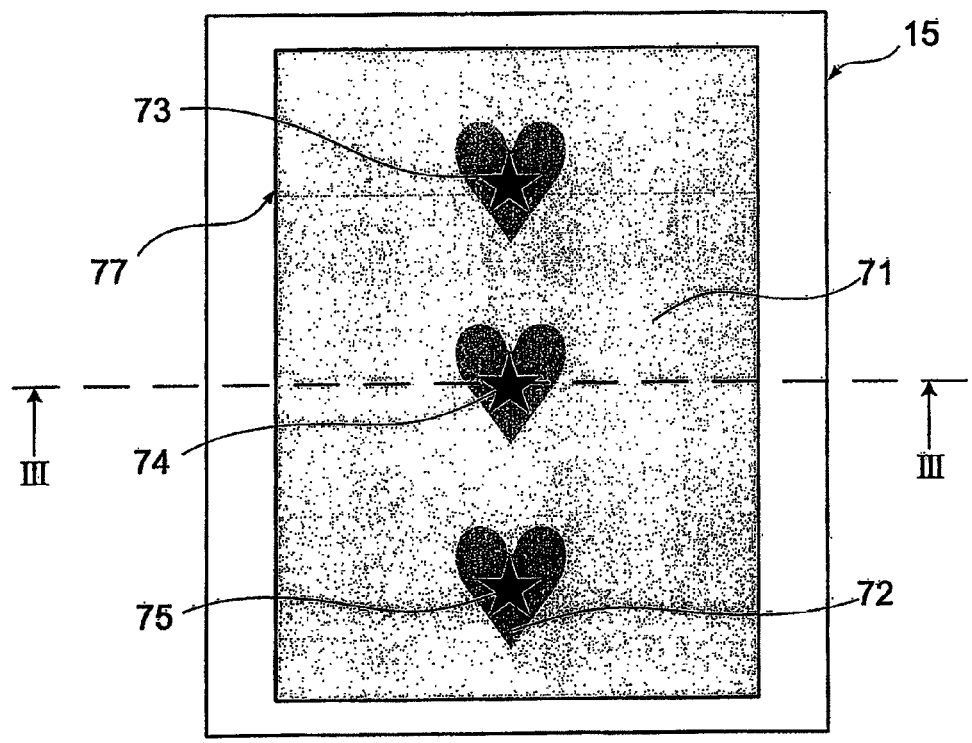
FIG. 7 is a plan view of the main portion of the third embodiment in accordance with this invention.
Figure 8:
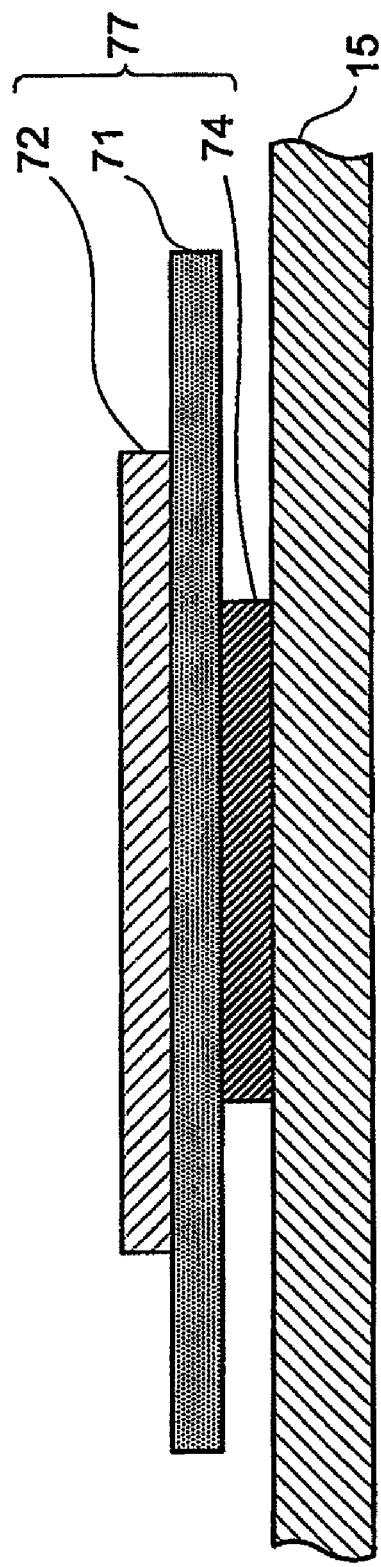
FIG. 8 is a sectional view taken along the line III-III of FIG. 7.

In the same way, FIG. 7 shows a main portion of a third embodiment in accordance with this invention, and in particular, it is a plan view of a water content indicator 77 in accordance with a modified embodiment of the water content indicator 76, and FIG. 8 is a sectional view taken along the line of FIG. 7.

As illustrated, the water content indicator 77 is similar to the water content indicator 76 in regards to the structure constituted by the hydrophilic resin coating layer 71 and the information mark 72 having the same shape and thickness, however, as shown in FIG. 8, it is different from the water content indicator 76 in regards to the printed surfaces 73, 74 and 75 which are provided between the water vapor permeable waterproof sheet 15 and the hydrophilic resin coating layer 71 at positions corresponding to the arranged positions of the respective information marks 72 by a general ink, that is, an ink which is not discolored even if it is brought into contact with the water content by the same printing system mentioned above. These printed surfaces 73, 74 and 75 are formed by the same color ink or different color inks relative to each other. In this case, since a capability of the ink is lowered if different inks are mixed, the mixed ink is not preferable.

Further, in this embodiment, a flat surface shape of the printed surfaces 73, 74 and 75 are mark of star-shaped, however, the mark can be optionally changed as mentioned above.

In accordance with the water content indicator 77 mentioned above, although each of the information marks 72 is discolored by being decolored if the excreted urine is brought into contact with the water content indicator 77, the printed surfaces 73, 74 and 75 are not changed. Accordingly, in the case of viewing from the outer side, only the printed surfaces 73, 74 and 75 remain, and the pattern of the print appears to be changed between after and before passing urine, whereby it is possible to instantaneously and securely inform the user of the excretion.

With respect to industrial applicability, for example, it goes without saying that this invention is not limited to the pants type disposable paper diaper, but can be widely applied to the other absorbent articles such as the sanitary napkin, the urine remaining pad and the like in addition to a tape type disposable paper diaper.

What is claimed is:

1. An absorbent article comprising, in integral formation, at least, a rectangular liquid permeable top sheet, an absorbent element including an absorbent covered with a crepe paper, a rectangular water vapor permeable waterproof sheet, and a rectangular liquid impermeable back sheet in this order, the absorbent article further comprising:
on a first portion of the water vapor permeable waterproof sheet, a water content indicator coating layer provided between the water vapor permeable waterproof sheet and the absorbent element,
the water content indicator coating layer comprising a hydrophilic resin coating layer and a layer of an information mark provided on an inner surface of the hydrophilic resin coating layer, and
wherein a permeability of the first portion of the water vapor permeable waterproof sheet and the hydrophilic resin coating layer is lower than a permeability of a second portion of the water vapor permeable waterproof sheet on which the hydrophilic resin coating layer is not provided on the water vapor permeable waterproof sheet.

2. The absorbent article as set forth in claim 1, wherein the water vapor permeable waterproof sheet is constituted by a sheet material in which a water vapor permeability on the basis of JIS Z-0208 method of test is 7000 g/m2/24 h or more.

3. The absorbent article as set forth in claim 1, wherein the hydrophilic resin coating layer and the information mark layer have substantially the same shape, and wherein the information mark layer and the hydrophilic resin coating layer have a thickness of 1 μm to 20 μm.

4. The absorbent article as set forth in claim 3, wherein the hydrophilic resin coating layer covers an entirety of the information mark layer when viewed from the liquid impermeable back sheet.

5. The absorbent article as set forth in claim 1, wherein the information mark layer is discolored when exposed to water.

6. The absorbent article as set forth in claim 1, wherein the hydrophilic resin coating layer comprises an ultraviolet absorbent, ultraviolet scattering agent, light stabilizer, or antioxidant.

7. The absorbent article as set forth in claim 1, wherein the hydrophilic resin coating layer and the water content indicator coating layer are arranged as strata.

8. The absorbent article as set forth in claim 1, wherein the water vapor permeable waterproof sheet and the liquid impermeable back sheet are adhered to each other with an adhesive.

* * * * *